US00PP11048P

United States Patent [19]

Zary

[11] Patent Number: Plant 11,048

[45] Date of Patent: Aug. 31, 1999

[54] HYBRID TEA ROSE PLANT NAMED 'JACVAL'

[75] Inventor: Keith W. Zary, Thousand Oaks, Calif.

[73] Assignee: Bear Creek Gardens, Inc., Medford, Oreg.

[21] Appl. No.: 09/024,210

[22] Filed: Feb. 17, 1998

[51] Int. Cl.[6] ..... A01H 5/00

[52] U.S. Cl. ..... Plt./137

[58] Field of Search ..... Plt./137, 138, 148

*Primary Examiner*—Howard J. Locker

*Attorney, Agent, or Firm*—Klarquist Sparkman Campbell Leigh & Whinston, LLP

[57] ABSTRACT

Hybrid tea rose having large, pure pink flowers of good hybrid tea flower form and moderate fragrance, strong vigorous growth and foliage resistant to powdery mildew.

1 Drawing Sheet

The present invention relates to a new and distinct variety of rose plant of the hybrid tea class which was originated by me by crossing an unnamed coral pink hybrid tea seedling, the parentage of which is 'JAColite' (U.S. Plant Pat. No. 4,167) × Silver Jubilee (not patented), with 'JACdis' (U.S. Plant Pat. No. 3,423).

The primary objective of this breeding was to produce a new rose variety having combine the strong growth, glossy, healthy foilage and large flowers of the unnamed seedling parent with the very good hybrid tea flower form, pure pink flower color and fragrance of the male parent. The objective was substantially achieved, along with other desirable improvements, as evidenced by the following unique combination of characteristics that are outstanding in the new variety and that distinguish it from its parents, as well as from all other varieties of which I am aware:

1. Good hybrid tea flower form;
2. Pure pink flower color;
3. Large flowers, borne one per stem;
4. Strong, vigorous, upright growth;
5. Resistance to powdery mildew;
6. Moderate fragrance.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed coral pink hybrid tea seedling, the parentage of which is 'JAColite' (U.S. Plant Pat. No. 4,167) × 'Silver Jubilee' (not patented).

*Pollen parent.*—'JACdis' (U.S. Plant Pat. No. 3,423).

Classification:

*Botanical.*—*Rosa hybrida*.

*Commercial.*—Hybrid tea.

FLOWER

Observations made from specimens grown in a greenhouse environment at Somis, Calif. from February, 1996 to October, 1997.

Blooming habit: Recurrent.

Bud:

*Size.*—1¾" long when the petals start to unfurl.

*Form.*—the bud form is long, pointed ovoid.

*Color.*—When sepals first divide, bud color is Red Group 55C. When half blown, the upper sides of the petals are Red Group 55C and the lower sides of the petals are Red Group 55C.

*Sepals.*—Color: Green Group 138B. Surface texture: Covered in fine hairs. There are three lightly appendaged sepals. There are two unappendaged sepals with hairy edges.

*Receptacle.*—Color: Green Group 137D. Shape: Funnel. Size: Medium (5/16"×3/16"). Surface: Smooth.

*Peduncle.*—Length: Medium (3 to 3½"). Surface: Smooth. Color: Medium green. Strength: Stiff, erect.

Bloom:

*Size.*—Large. Average open size is 4 to 4½".

*Borne.*—Singly.

*Stems.*—Long (18–22"), strong.

*Form.*—When first open: High centered. Permanence: Outer petals curl back.

*Petalage.*—Number of petals under normal conditions: 25–30.

*Color.*—The upper sides of the petals are Red Group 55C. The reverse sides of the petals are Red Group 55C. The base of each petal has a small (3/32"×3/32") Yellow Group 3C half moon at the point of attachment. The major color on the upper sides is Red Group 55C.

*Variegations.*—Occasional greenish white streak on the guard petals.

*Discoloration.*—At the end of the first day: No change. At the end of the third day: No change. General fading at day six or seven to Red Group 55D followed by petal drop.

*Fragrance.*—Moderate.

Petals:

*Texture.*—Thick.

*Shape.*—round to slightly deltoid.

*Form.*—Tips slightly recurved, edges slightly undulating.

*Arrangement.*—Imbricated. Petaloids in the center are few.

*Persistence.*—Petals drop off cleanly before drying.

*Lastingness.*—On the plant: Long (7–8 days). As a cut flower: Long (9–10 days).

Reproductive parts:

*Anthers.*—Size: Medium Quantity: Many. Color: Yellow. Arrangement: Regular around styles.

*Filaments.*—Color: Yellow.
*Pollen.*—Color: Lemon yellow.
*Styles.*—Color: Red.
*Stigmas.*—Color: Greenish white.

Plant:
*Form.*—Bush.
*Growth.*—Vigorous; upright; branching; Height is five to five and one half feet, width is four feet.

Foliage: Number of leaflets on normal mid-stem leaves: Five or seven.
*Size.*—Large (6 to 6½"–4 to 4½").
*Quantity.*—Abundant.
*Color.*—New foliage: Upper and lower side: Greyed Red Group 178A. Old foliage: Upper side: Green Group 139A. Lower side: Green Group 139C.

Leaflets:
*Shape.*—Pointed oval.
*Texture.*—Upper side: Leathery.
*Edge.*—Serrated.
*Serration.*—Single, small.
*Petiole rachis.*—Color: Reddish when young, then green.
*Petiole underside.*—Smooth with occasional prickles.
*Stipules.*—Medium (⅜"–½"), bearded.
*Disease resistance.*—Resistant to mildew under normal growing conditions at Somis, Calif.

Wood:
*New wood.*—Color: Light green. Bark: Smooth.
*Old wood.*—Color: Green. Bark: Smooth.

Prickles:
*Quantity.*—On main canes from base: Many. On laterals from main canes: Many.
*Form.*—Short, hooked downward.
*Color when young.*—Red.

Small prickles:
*Quantity.*—On main stalks: Few. On laterals: Few.
*Color.*—Brown.

I claim:

1. A new and distinct variety of rose plant of the hybrid tea class substantially as herein shown and described, characterized particularly as to novelty by its large, pure pink flowers of good hybrid tea flower form borne one per stem; and having moderate fragrance; its strong, vigorous, upright growth with foliage resistant to powdery mildew.

* * * * *

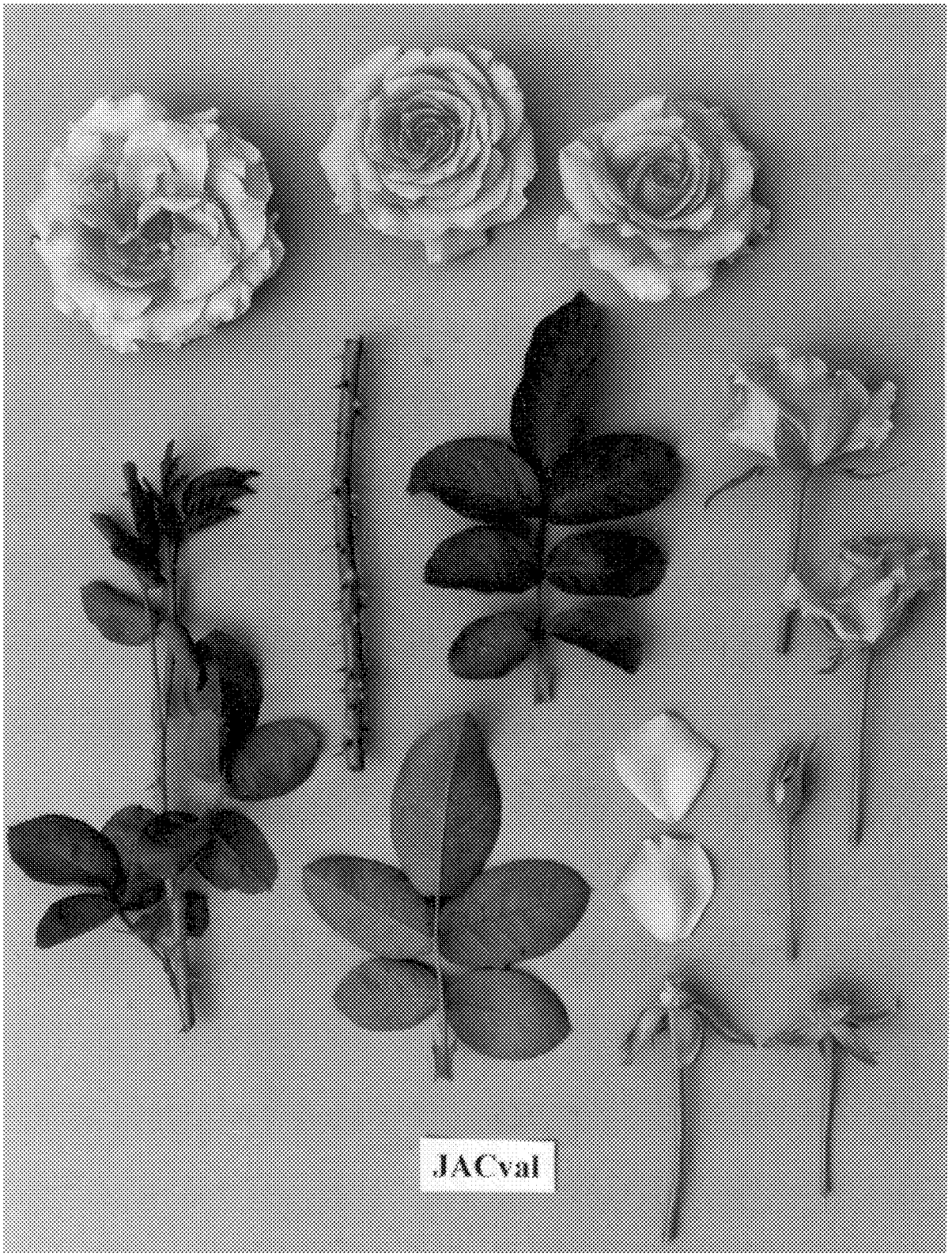
JACval